United States Patent [19]

Sarrine et al.

[11] Patent Number: 4,938,080
[45] Date of Patent: * Jul. 3, 1990

[54] AUTOMATIC PIPETTING APPARATUS

[75] Inventors: Robert J. Sarrine, Beaumont; Henry A. Garsee, Kountze, both of Tex.

[73] Assignee: Helena Laboratories, Inc., Beaumont, Tex.

[*] Notice: The portion of the term of this patent subsequent to May 9, 2006 has been disclaimed.

[21] Appl. No.: 361,700

[22] Filed: Jun. 1, 1989

Related U.S. Application Data

[63] Continuation of Ser. No. 242,378, Sep. 9, 1988, abandoned, which is a continuation of Ser. No. 89,025, Aug. 24, 1987, Pat. No. 4,827,780, which is a continuation of Ser. No. 853,201, Apr. 17, 1986, abandoned.

[51] Int. Cl.$^5$ ............................................. B01L 3/02
[52] U.S. Cl. ................................. 73/864.21; 204/299 R
[58] Field of Search .............. 73/863.31, 863.32, 863.01, 73/863.33, 864.21, 864.25; 204/299 R, 182.7, 182.8, 182.9; 422/102, 62, 69, 70, 55, 100, 56, 68.02, 68.08, 63, 67; 436/169; 210/198.3, 658; 435/815

[56] References Cited

U.S. PATENT DOCUMENTS

| | | | |
|---|---|---|---|
| 3,536,449 | 10/1970 | Astle | 73/863.32 |
| 3,616,387 | 10/1971 | Siebert et al. | 204/299 R |
| 3,902,852 | 9/1975 | Lemieux et al. | 73/863.32 |
| 3,915,856 | 10/1975 | Meyer | 210/198.3 |
| 4,478,094 | 10/1984 | Salomaa et al. | 73/863.32 |
| 4,827,780 | 5/1989 | Sarrine et al. | 73/864.21 |

FOREIGN PATENT DOCUMENTS 1032096 6/1966 United Kingdom ............ 210/198 C Primary Examiner—Robert Raevis
Attorney, Agent, or Firm—Dodge, Bush & Moseley

[57] ABSTRACT

An automatic pipetting apparatus is disclosed having a base on which is mounted a vertical frame supporting a row of positive displacement pipettes which are driven in the up or down direction by an electromechanical mechanism under microprocessor controls. The apparatus includes a base, a track and a carriage longitudinally movable beneath the row of pipettes. The carriage includes an independent translating and position signal generation mechanism. The carriage carries a tray which includes sample chambers, a space to receive a microporous electrophoresis support medium, such as a cellulose acetate strip, a wash well, rinse well and a space to receive blotting paper. The pipettes include a barrel and a plunger capable of aspirating and dispensing from 0.5 to 5 μl of liquid. The barrels move up and down with respect to the base by means of another independent translating and signal generating mechanism. The barrels may be easily replaced from the mechanism if they become damaged or worn from many operating cycles. The apparatus under microprocessor program control, washes, rinses, blots the barrels before and after each application or engagement of the barrels with a liquid or contaminant.

2 Claims, 10 Drawing Sheets

FIG.1
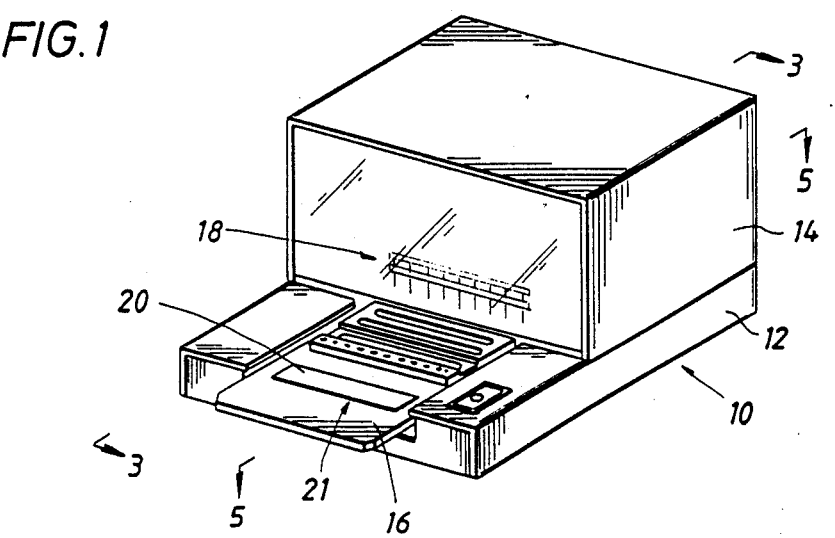
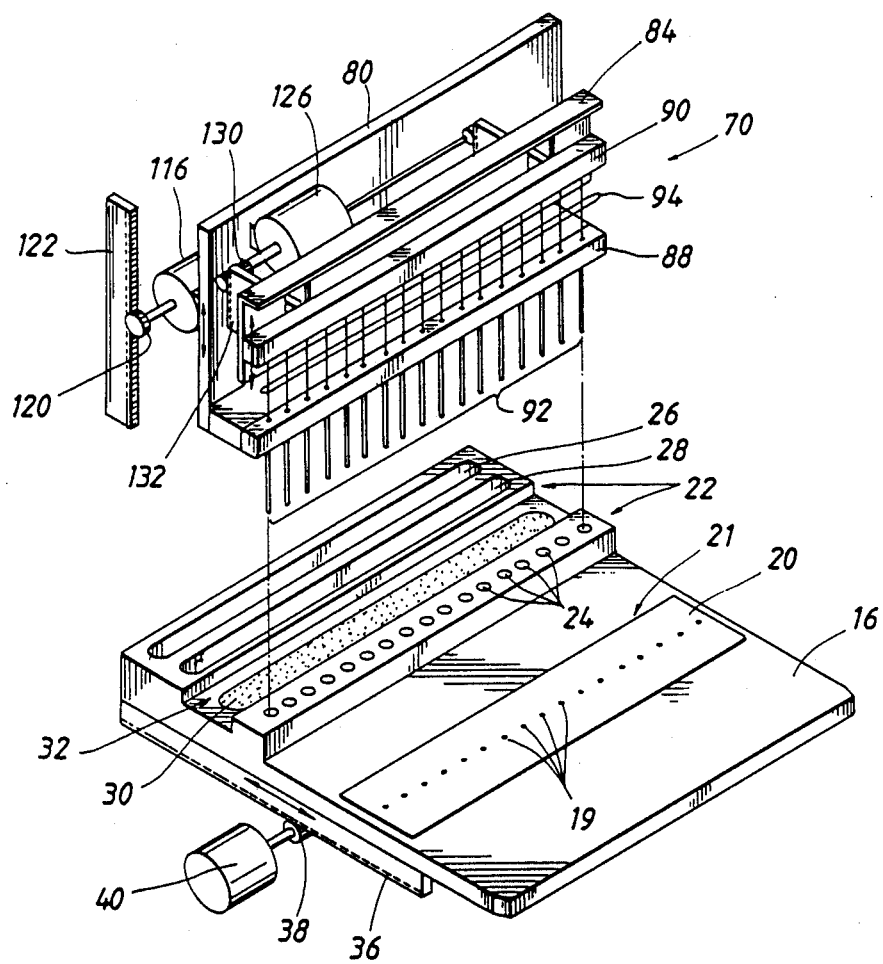
FIG.2

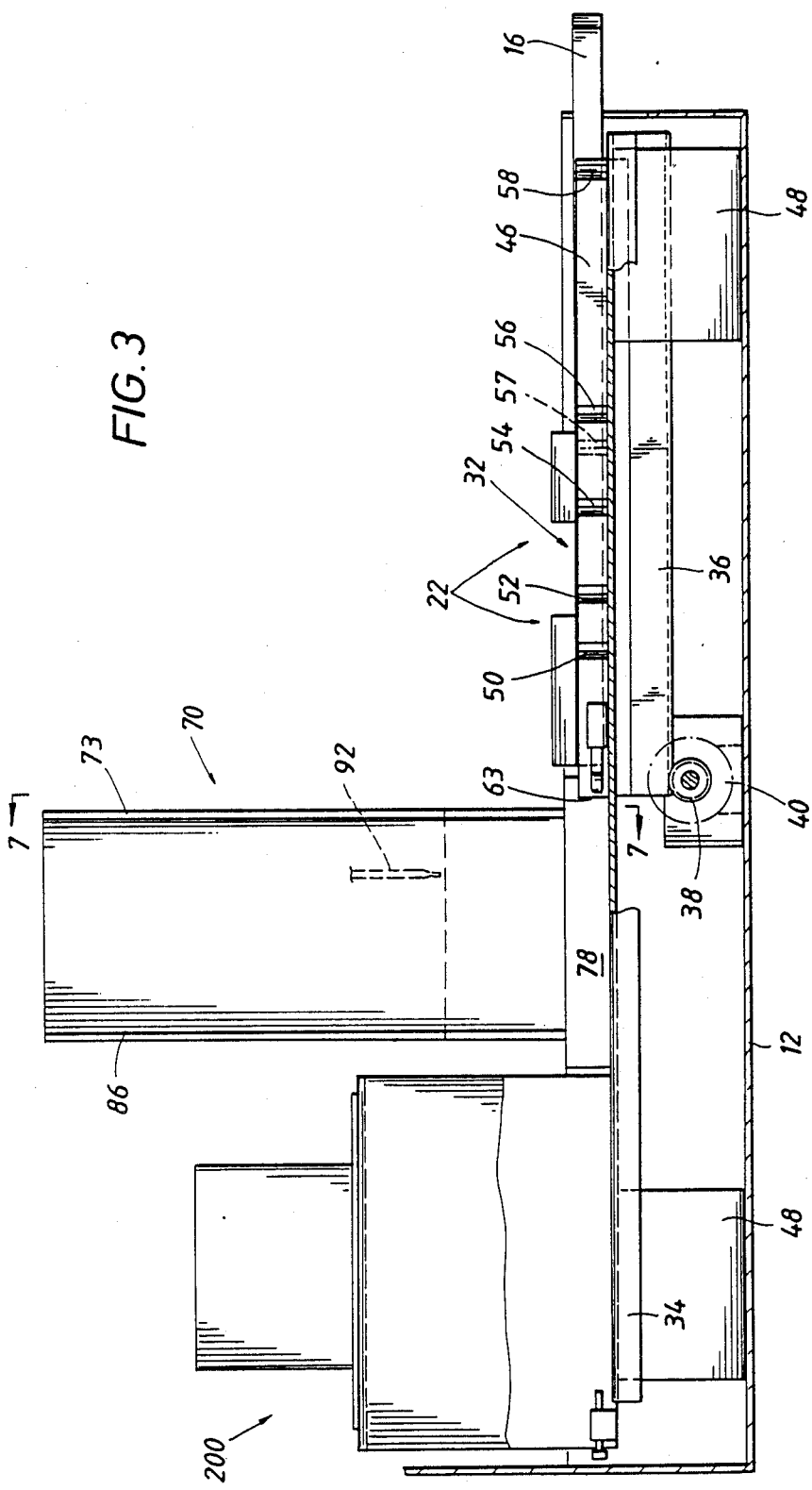
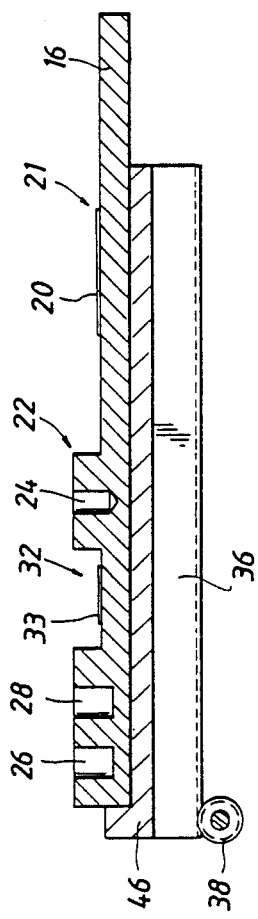
FIG. 3
FIG. 4

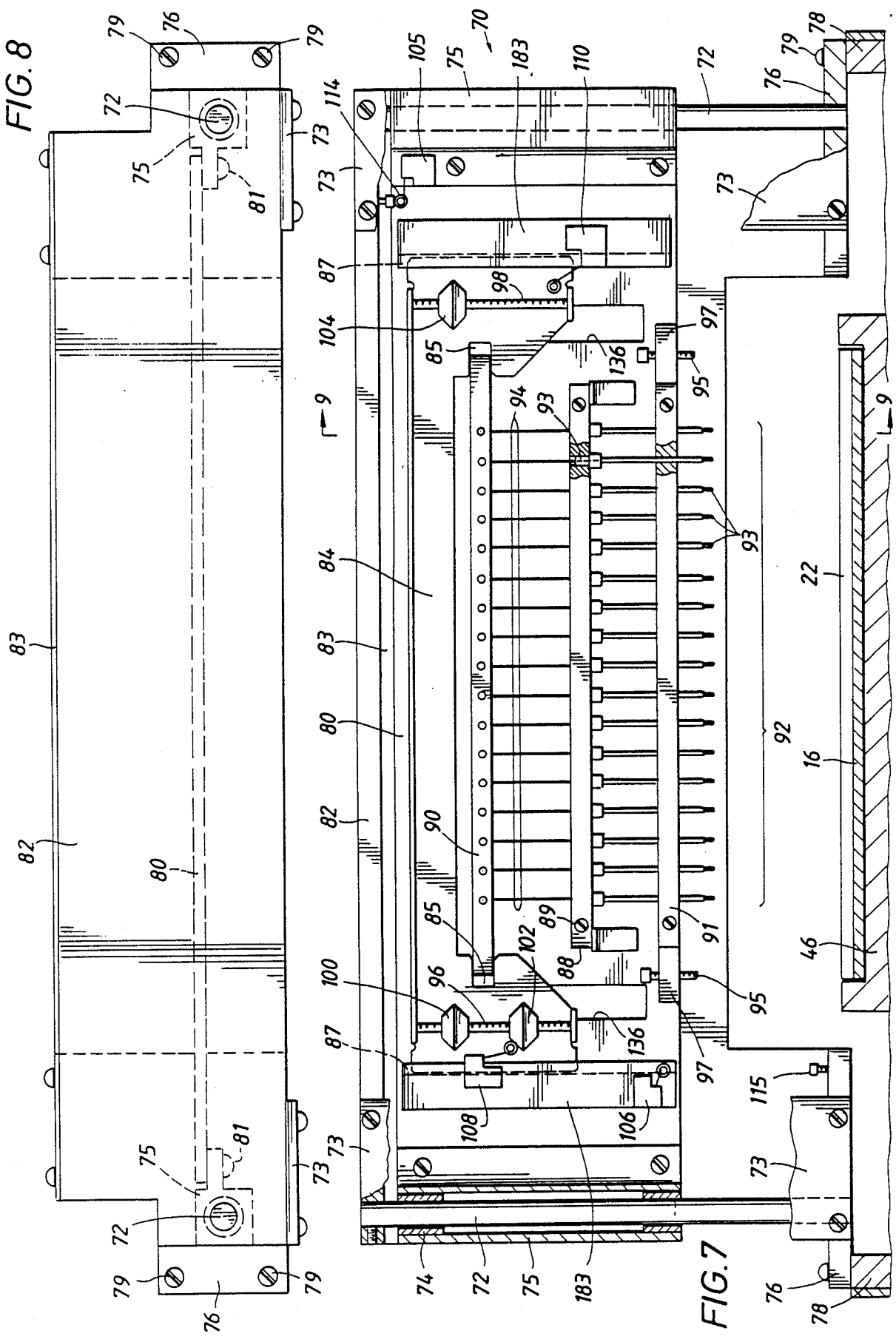

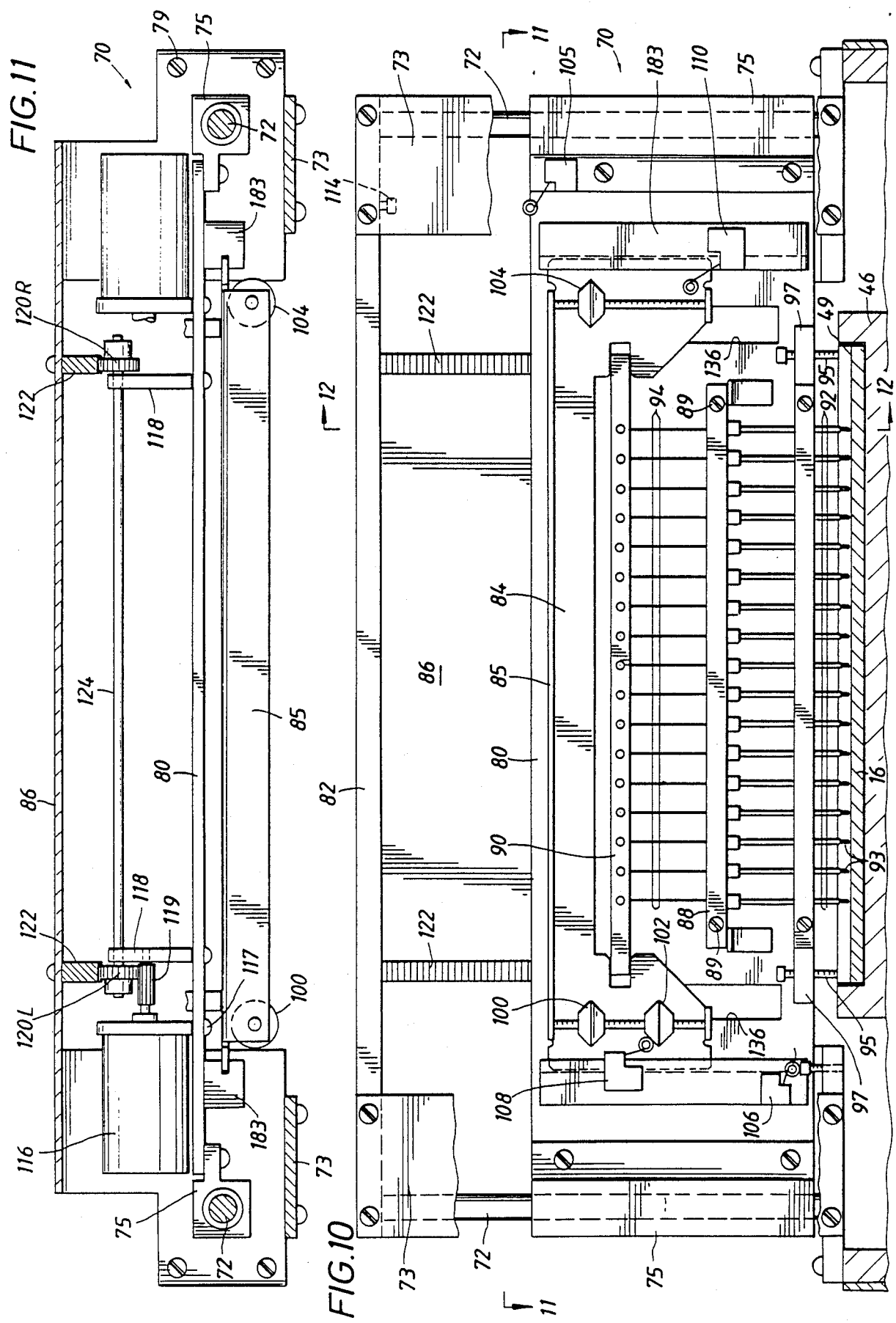

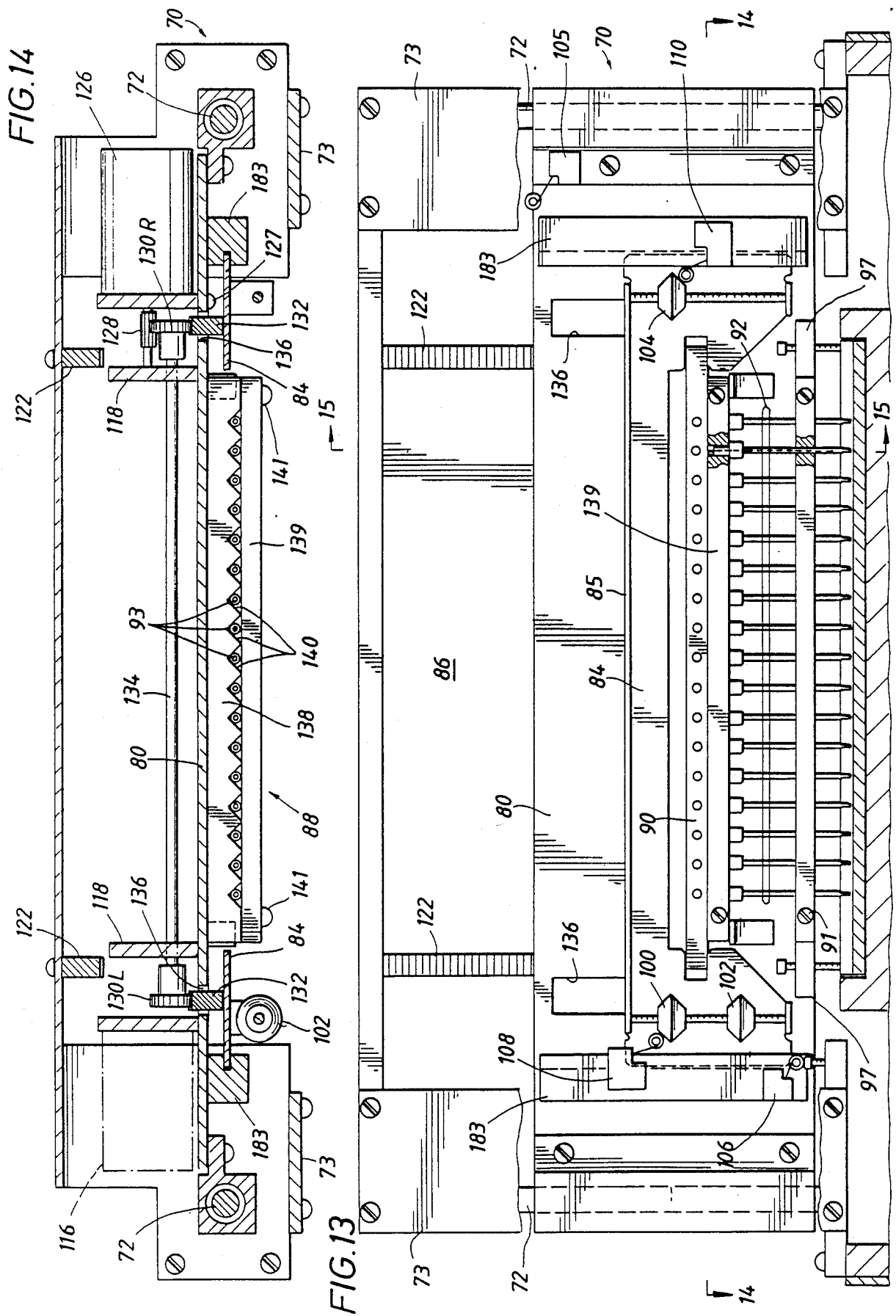

AUTOMATIC PIPETTING APPARATUS

This application is a continuation, of application Ser. No. 242,378, filed 9/9/88, now abandoned, which is a continuation of application Ser. No. 089,025, filed 8/24/87, now U.S. Pat. No. 853,201, Apr., 17, 1986 now abandoned.

BACKGROUND OF THE INVENTION

1. Field of the Invention

This invention is related in general to the field of applying fluid samples to analysis strips. In particular, this invention relates to an automatic pipetting apparatus for applying multiple fluid samples to a microporous support medium such as a cellulose acetate or agarose strip which may be used in the field of zone electrophoresis and with other separation techniques including the field of thin layer chromatography. Zone electrophoresis is the science of moving charged particles in an electric field through a solid or semi-solid medium. The technique is most commonly used in medical research and medical laboratories for analyzing various blood proteins.

2. Description of the Prior Art

In the electrophoresis technique, a blood or other fluid sample is applied to a support medium which is then subjected to an electric field so as to separate the components of the sample. The support media used in the electrophoresis process includes cellulose acetate, agar, agarose and acrylamide gels. In laboratory work it is desirable that a plurality of samples be applied to the support medium such that each of the samples may be subjected to the electric field at the same time.

The samples may be applied to the support medium one at a time in serial fashion with a hand pipetter, but the hand pipetter must be rinsed with a cleansing agent and blotted before a new sample is aspirated and then applied to the strip.

Applicators have been designed to apply fluid samples simultaneously or in "parallel" to the strips. Such applicators are described at page 61 of the General Products Catalog for 1984–1985 of Helena Laboratories with offices in Beaumont, Texas. Such applicators may apply eight, twelve or more samples to a microporous support medium and have the advantage of making the electrophoresis technique easier and more reproducible.

The applicators known prior to this invention however have been essentially non-automatic applicators and required cleaning of the applicator tips after each application to the support medium.

Automatic dispensing systems are known in the prior art. For example, a system sold under the trademark "Well Washers" of BioTech Instruments, Inc. of Burlington, Vermont provides an alignment mechanism by which a row of eight or twelve barrels may be positioned above one of a plurality of rows of washing vials or wells. Automation in the system provides selection of dispensing fill volumes, soaking times and number of wash cycles.

None of the prior art however has provided an apparatus for automatically filling a plurality of pipetters from a respective plurality of fluid chambers and then precisely applying such fluid samples from each pipette to a support medium. Another disadvantage of the prior art systems is that there has been no means for automatically washing and cleaning the barrels during each cycle time so as to prevent contamination of each of the barrels during application of a new plurality of fluid samples to a new support medium.

Another disadvantage of the prior art is that there has been no means for precisely automatically applying a very small amount—of the order of one micro liter of sample liquid—to a support medium.

Another disadvantage of the prior art is that there has been no means for precisely automatically diluting a very small amount—of the order of one micro liter—of sample fluid with a diluting liquid, and precisely applying a very small amount of the diluted sample to a support medium.

Identification of Objects of the Invention

It is therefore a primary object of the invention to provide an automatic pipetter apparatus for aspirating from a plurality of sample chamber wells into a corresponding plurality of pipetters and then applying such samples precisely to a microporous support medium to be used in electrophoresis or thin layer chromatography.

It is a further object of the invention to provide an automatic pipetting apparatus which not only aspirates and dispenses sample fluids onto a support medium strip such as cellulose acetate or agarose, but also flushes, cleanses, rinses and blots the tips of the barrels with an appropriate cleaning fluid before and after each application of the sample fluid to the support medium.

It is another object of the invention to provide an automatic pipetting apparatus by which positive displacement pipette barrels and plungers are controlled to precisely apply a very small sample of fluid to a support medium.

It is another object of the invention to provide automatic pipetting apparatus for precisely automatically diluting a very small amount of sample fluid with a diluting liquid and precisely applying a very small amount of the diluted sample to the support medium.

SUMMARY OF THE INVENTION

The objects identified above as well as other advantages and features of the invention are provided in an automatic pipetting apparatus which generally includes a base and a sample plate disposed on the base and a pipette frame including a vertical support for supporting the frame from the base above the sample plate. The sample plate includes a row of individual liquid sample chambers and a lateral application space longitudinally separated from the liquid chamber row. The lateral application space is adapted to receive a microporous support medium. A mounting plate is carried by the pipette frame.

The apparatus includes translation means for effecting relative longitudinal movement of the pipette frame and sample plate, and vertical translation means for effecting relative vertical movement of the mounting plate and the sample plate.

A plurality of microsyringe barrels are removably secured to the mounting plate. The barrels are spaced corresponding to the spacing of the liquid chambers of the sample plate. A plurality of micro-plungers are provided, one each movably disposed in one of the barrels. A plunger translation means is provided for moving the plunger vertically within the barrels.

Signalling means are provided for generating longitudinal signals representative of the relative longitudinal orientation of the pipette frame with respect to the sample plate, for generating mounting plate signals representative of the vertical orientation of the mounting plate relative to the sample plate and for generating plunger signals representative of the orientation of the plungers relative to the barrels.

A programmed digital computer is provided responsive to the longitudinal signals, the mounting plate signals and to the plunger signals for generating a sequence of control signals to the longitudinal translation means, to the vertical translation means and to the plunger translation means to aspirate a predetermined amount of liquid from the sample chambers into the respective pipette barrels, and to apply the liquid samples in the barrels onto corresponding spaces or "spots" on the microporous support medium when placed on the lateral application space of the sample plate.

One embodiment of the invention includes a base having a track disposed longitudinally on it. A carriage is longitudinally movably disposed on the track means and carries a sample plate which is removably disposed on the carriage. The carriage plate includes a lateral row of individual liquid sample chambers and a lateral application space which is longitudinally separated from the liquid chamber row. The lateral application space is adapted to receive a microporous support medium such as a cellulose acetate or agarose strip used in electrophoresis or thin layer chromatography.

A pipette assembly is mounted vertically on the base above the carriage and the sample plate. The pipette assembly includes vertical mounting posts separated laterally from each other and secured to the base. A mounting plate assembly is slidably guided by the posts and is disposed laterally with respect to the sample plate.

The mounting plate assembly includes a mounting plate having slidable guides disposed about the posts. A pipette bar is fixed to the mounting plate. A plurality of microsyringe barrels are provided in a row on the pipette bar with their heads secured thereto. The microsyringe barrels are spaced corresponding to the spacing of the liquid chambers on the plate. The barrels are hollow, each barrel having a lower tip.

A plunger bar is vertically movably disposed above the tip bar and has a plurality of micro-plungers secured thereto. Each of the micro-plungers are movably disposed within a corresponding barrel of the microsyringes. A plunger actuator plate carried by the mounting plate is vertically movable with respect to the mounting plate. The actuator plate is removably secured to the plunger bar.

Translation and signalling means are provided for moving the carriage longitudinally forward and backward beneath the mounting plate assembly and generating carriage position signals indicative of the carriage position. A translation and signalling means is provided for moving the mounting plate assembly up and down with respect to the base and generating mounting plate position signals indicative of the mounting plate position. A translation and signalling means for moving the plunger bar up and down with respect to the mounting plate and generating plunger bar position signals indicative of the plunger bar position is provided.

A programmed microcomputer is provided responsive to the carriage position signals, to the mounting plate position signals, and to the plunger bar position signals for generating a sequence of control signals to the translation means for moving the carriage, the translation means for moving the mounting plate, and the translation means for moving the plunger bar so as to aspirate a first predetermined amount of liquid from the sample chambers into the respective pipette barrels and then to apply the liquid in each of the pipette barrels onto corresponding spaces of the support medium when placed on the lateral application space of the sample plate.

The sample plate includes a wash well and waste well longitudinally spaced form each other and from the sample chamber. The programmed computer generates a further sequence of control signals to the translation means before aspirating liquid from the sample chambers to draw a second predetermined amount of rinse liquid from the wash well into the respective pipette barrels and then to discharge that rinse liquid into the waste well.

The apparatus further provides the sample plate with a longitudinal blotting space for applying a lateral blotting paper strip where the blotting space is longitudinally separated from the sample chamber row, the wash well, the waste well and the lateral application space. The programmed computer generates a further sequence of control signals to the translation means after discharging the wash liquid into the waste well so as to blot the lower tips of the barrels on the blotting paper strip.

Preferably, the sample plate includes a raised portion and a lower portion where the row of individual liquid sample chambers and the wash well and the waste well are disposed on the raised portion and the lateral application space and the blotting space are disposed on the lower portion.

The sample plate may include a row of liquid dilution wells longitudinally spaced from the sample chambers. The programmed computer includes a program, actuated by a dilution signal, for automatically controlling the apparatus for diluting the samples aspirated to the microsyringe barrels with dilution fluid and mixing the sample and dilution fluid in each of the dilution wells before mixed diluted sample fluid is applied to the spots of the support medium.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 1 shows a perspective view of one embodiment of the automatic pipetting apparatus of the invention with a sample plate secured thereto and its cover attached;

FIG. 2 is a schematic illustration of the invention showing the functional relationship between the sample plate with its sample chambers, wash well, waste well and a longitudinal application space with a microporous support medium secured thereto beneath a pipette assembly in which individual pipette barrels are moved as a unit up and down and a plunger bar secured to plungers which are moved up and down with respect to the barrels;

FIG. 3 is a side view partially cut away and in section with the cover removed and taken from the view along lines 3—3 of FIG. 1;

FIG. 4 is a cross-section of the carriage and the sample plate;

FIG. 7 is a forward looking view taken along lines 7—7 of FIG. 3 and shows partially broken away, partially cross-sectional parts of the pipette assembly slidably mounted on posts secured to the base and including a mounting plate which moves up and down with respect to the base and carrying a row of barrels of individual pipettes and an actuator plate movable vertically with respect to the mounting plate for moving a plunger bar vertically for moving individual plungers within the barrels of each of the pipettes;

FIG. 8 shows a top view of the pipette assembly showing in dashed lines the mounting plate of the pipette assembly;

FIG. 10 is a similar view to that of FIG. 7 but shows the mounting plate having been translated to a lower position but with the plunger bar remaining in an upward position whereby the tips of the pipetters are in a downward position, but the plungers are extended upwardly from each of the barrels of the pipettes;

FIG. 11 is a top cross-sectional view taken along lines 11—11 of FIG. 10 and illustrates the motor and rack and pinion system by which the mounting plate is moved up and down with respect to the base;

FIG. 13 is a view similar to that of FIGS. 7 and 10 but illustrated the plunger actuator plate and plunger bar moved downwardly with respect to the mounting plate thereby forcing the plungers associated with each of the pipetters into their barrels and forcing any fluid previously aspirated into the barrels out the tips of the barrels;

FIG. 14 shows a cross-sectional view taken along lines 14—14 of FIG. 13 and illustrates the rack and pinion system by which the actuator plate and the plunger bar secured thereto is moved up and down with respect to the mounting plate;

DESCRIPTION OF THE INVENTION

Figure 2A:
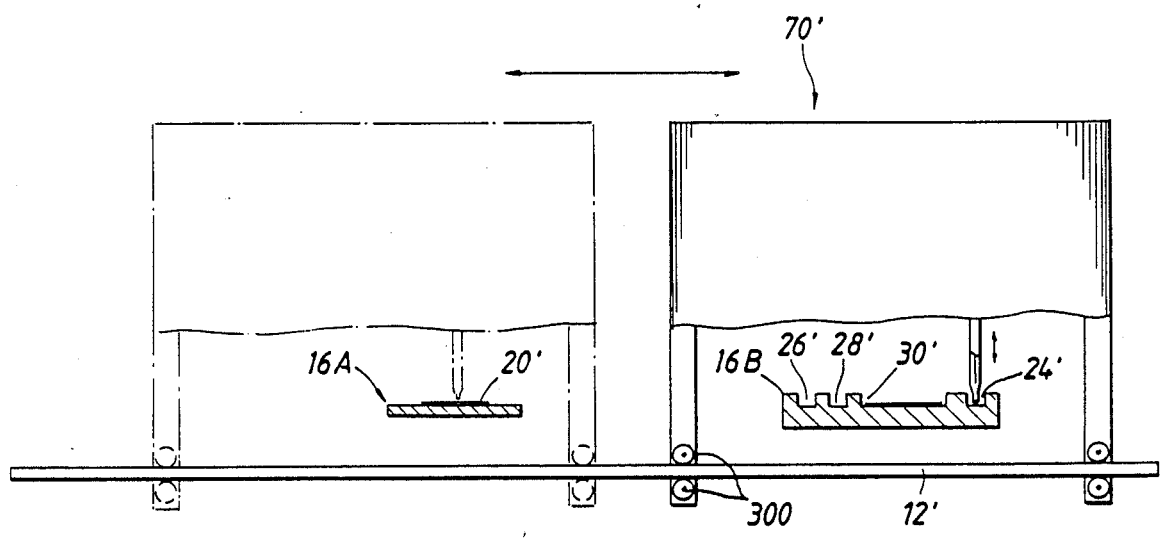
FIG. 2A schematically shows another embodiment of the invention where the mounting plate includes two stationary units and the pipette frame is longitudinally movable with respect to the plate.

FIG. 1 illustrates in a perspective view the automatic pipetting apparatus 10 according to the invention. The apparatus includes a base 12 on which a sample plate 16 is movably supported. The sample plate includes a space 21 for securing a microporous support medium 20 such as a cellulose acetate or agarose strip used in the field of zone electrophoresis or other separation techniques including the field of thin layer chromatography. A cover 14 is provided behind which a pipette head 18 is shown.

FIG. 2 is a schematic illustration of the essential mechanical elements of one embodiment of the invention with the base and the cover removed. None of the mounting apparatus is shown in FIG. 2 so as to simplify the explanation of the relationship of the sample plate 16 to the pipette assembly 70. The translational means are shown in a functional way rather than in actual mechanical detail which will be shown in detail in the figures and discussion below.

The sample plate 16 as shown includes a row of sample chambers 24 as well as a wash well 26, rinse or "waste" well 28 and a longitudinal space 21 on which a microporous support medium 20 is removably secured. The sample chambers 24, the rinse well 28 and the wash well 26 are provided on raised portions 22 of the sample plate. If desired, a plastic cup may be provided in each of sample chambers 24. A notch 32 between the rinse well 28 and the sample chambers 24 is provided at substantially the same vertical level as the sample application space 21 on which the support medium 20 is secured.

As illustrated in FIG. 2, the various regions of the sample plate are longitudinally distinct <.yet the lateral spacings between the sample chambers 24 corresponds to the application spots !9 on the support medium 20 which is indicative of the fact that the barrels 92 of the pipetters are arranged in a row corresponding to the chambers 24. Liquid from those chambers is aspirated by the automatic pipetting apparatus and is applied in a similar row on the spots 19 of the microporous support medium 20.

It is advantageous to provide the sample chambers 24, waste well 28 and wash well 26 in raised portions of the sample plate so that the mounting plate of the pipette assembly need only go down to a common downward position during all wash, waste, blot, sampling and application operations. However, it would be obvious to one of ordinary skill in the art that other arrangements could be provided especially where different levels of the mounting plate could be provided in the translation and signalling apparatus for controlling the mounting plate 80. A detailed discussion of such translation and signalling apparatus for controlling the mounting plate 80 is discussed below.

The schematic illustration of FIG. 2 shows that the sample plate 16 is translated in forward and rearward directions beneath the pipette assembly 70 by virtue of the motor 40 turning a pinion 38 having its gears in engagement with those of rack 36. As the shaft of the motor 40 turns, the sample plate 16 carried by the rack 36 moves back and forth beneath the Pipette assembly 70.

Turning now to the pipette assembly 70 shown in FIG. 2, a mounting plate 80 is translated upwardly and downwardly by means of mounting plate motor 116 having its pinion 120 engaging a rack 122. Thus, the entire mounting plate 80, and the microsyringe barrels 92 attached to the pipette bar 88 which is secured to the mounting plate 80, moves up and down in accordance with the turning of the mounting plate motor 116. Similarly, the plungers 94 which are attached to plunger bar 90 and actuator plate 84 are moved up and down with respect to mounting plate 80 by operation of the turning of actuating plate motor 126 and its pinion 130 engaging actuator rack 132. For purposes of illustration, the actuator plate motor 126, its pinion 130 and the actuator plate rack 132 are shown on the forward side of mounting plate 80, but the actual apparatus illustrated in the subsequent figures is to the rearward side of the mounting plate 80 through slots in it.

FIG. 2 therefore shows all of the essential elements as far as the translation of the sample plate 16 backward and forward beneath the microsyringe barrels 92 and illustrates the upward and downward translation means of the mounting plate 80 and the microsyringe barrels 92, and the upward and downward motion of the plungers 94 and the plunger bar and actuator plate with respect to the mounting plate 80.

FIG. 2A schematically illustrates an alternative embodiment of the invention where the sample plate remains immovable with respect to the base with the pipette assembly 70' being mounted on rollers 300 for longitudinal translation. FIG. 2A illustrates that the sample plate may include two units, an application plate unit 16A and a fluid plate unit 16B. The sample plate unit 16A is adapted to removably secure a support strip 20' while the fluid plate unit 16B includes a row of sample chambers 24', a waste well 28', a wash well 26' and a blotting space 30'. The operation of the alternative embodiment is similar to that of the embodiment of FIG. 2 except that translation and signalling means are provided for longitudinally translating pipette assembly 70' with respect to the sample plate(s) 16A, 16B. Details of such translation and signalling means will be apparent to one of ordinary skill in this art by virtue of the detailed description of analagous translation and signalling means described below.

Figure 2B:
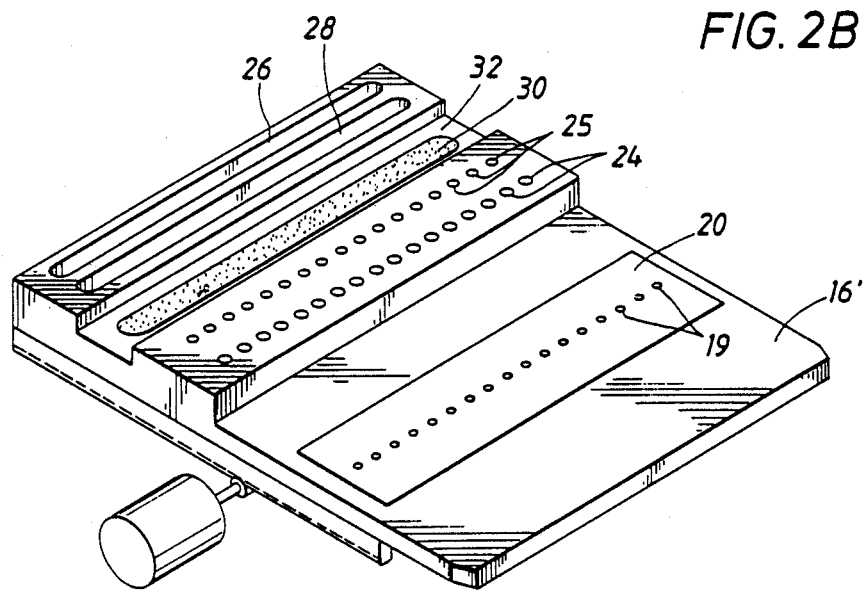
FIG. 2B is a perspective view of another embodiment of the sample plate further including a row of dilution wells.

FIG. 2B illustrates an alternative sample plate 16' which may include an additional row of dilution wells 25 in addition to the row of sample chambers 24, waste well 28, wash well 26 and blotting space 32. Explanation of the automatic diluting of sample fluid will be described below with reference to FIG. 2B.

FIG. 3 is a side view taken along lines 3—3 of FIG. 1 with a portion of track 34 cut away to show its construction. The tracks 34 are supported by track supports 48 which may also be seen in FIG. 5. The pipette assembly 70 is vertically supported from base mounting block 78 which is secured to the sides of the base 12 and is also further illustrated in FIG. 5. The pipette assembly 70 includes a back plate 86 and a front plate 73. One of the plurality of barrels 92 of the pipette assembly is shown in an upward position.

Figure 6:
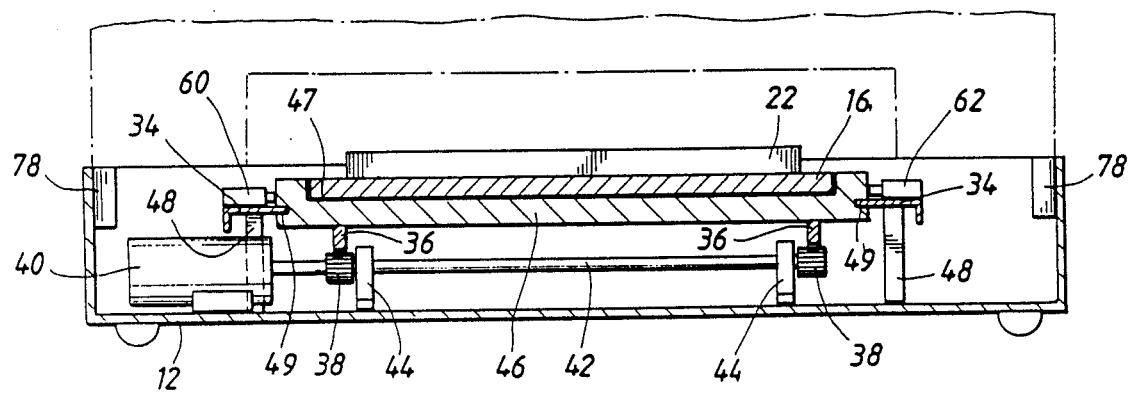
FIG. 6 is a cross-sectional view taken along lines 6—6 of FIG. 5 and shows the base, the carriage and sample plate according to the invention and further shows the translation and guiding means by which the track is moved forward and backward with respect to the pipetting assembly.

A carriage 46 is slidably movably disposed on track 34 as more clearly seen in FIG. 6. Racks 36 are secured to the carriage 46 and are movable with respect to the base 12 by means of the carriage motor 40 having its pinion 38 in engagement with rack gear 36.

Notches are provided along the left edge of the carriage 46. These notches cooperate with a trip switch to provide signals indicative of the longitudinal position of the carriage. The wash notch 50, rinse notch 52, blot notch 54, sample chamber notch 56, dilution chamber notch 57 (where the alternative sample plate 16' of FIG. 2B is used) and application notch 58 are illustrated in FIG. 3.

FIG. 4 illustrates a vertical cross-section through the carriage 46 and the plate 16 and shows the actual wash well 26, rinse well 28 and one of the sample chambers 24 on raised portion 22 of the plate 16. A notch 32 and a lateral application space 21 are illustrated on plate 16. Blotter paper 30 is shown in notch 32 while a microporous support medium 20 such as cellulose acetate or agarose is secured in lateral application space 21.

Figure 5:
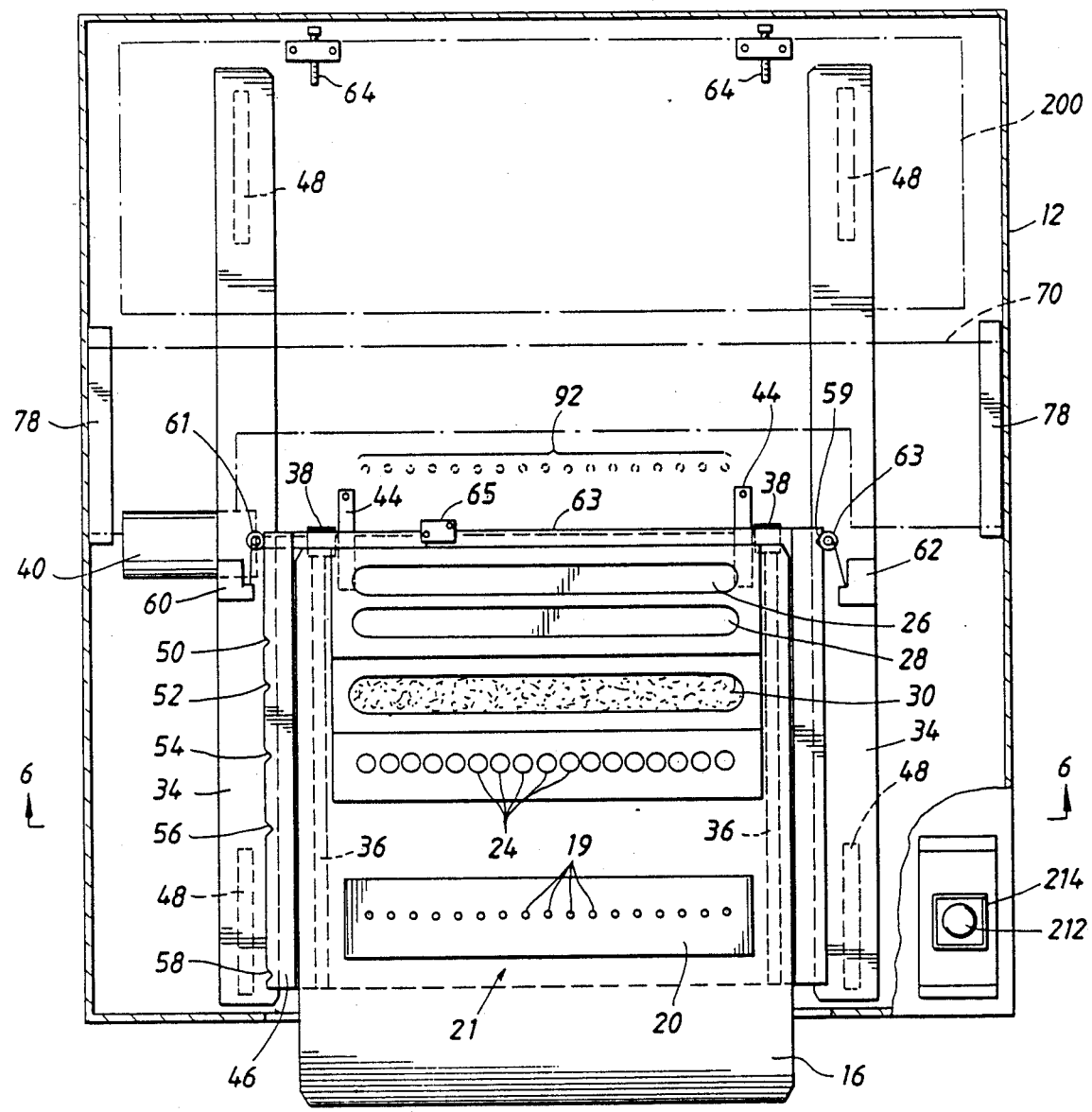
FIG. 5 is a downward looking view along lines 5—5 of FIG. 1 and shows the cross-section of the base at level 5—5 and the track, carriage and sample plates beneath the pipetting assembly.

FIG. 5 is a downward view taken along lines 5—5 of FIG. 1. Carriage 46 is shown supported by tracks 34 and movable in the rearward and forward directions by means of motor 40, pinion 38 and rack 36 as also illustrated in FIG. 6. The sample plate 16 is disposed in a valley or U-shaped cross-sectional structure 47 of carriage 46.

Position signalling notches on the sides of the carriage 46 cooperate with trip switch 60 and trip switch 62 fixed to tracks 34. Spring loaded rollers 61 and 63, respectively are forced against the longitudinal edges of sample plate 16 and into the notches as the carriage 46 moves past them. For example, the notches on the left hand side 46 include the wash notch 50, the waste notch 52, the blot notch 54, the sample chamber notch 56 and an application notch 58. The notches correspond to the longitudinal position of the wash well 26, waste well 28, blot paper 30, sample chambers 24 and application spots 19 when those wells, chambers and blotting and application spots are directly beneath the barrels of the pipettes 92.

When the carriage 46 moves rearwardly where the wash well 26 is directly beneath the barrels 92, the roller 61 moves into the notch 50 thereby tripping the trip switch 60 for signalling the microprocessor associated with electric module 200 (FIGS. 3 and 16) that the wash well is beneath the barrels 92. The trip switch 60 is likewise tripped when the roller 61 enters notches 50, 52, 54, 56 and 58 to signal the position of the respective other wells, chambers and spots beneath the barrels 92.

On the right hand side of the carriage 46 is notch 59 in which the roller 63 is shown. Trip switch 62 is thereby tripped to indicate that the carriage is at its maximum forward position. Trip switch 65 is mounted on the rear edge of carriage 46. Switch 65 closes when the rear edge of the plate 16 is in position and engages it thereby generating a signal that the plate 16 is properly in position on carriage 46. The stops 64 provide means for accurately longitudinally positioning application spots 19 beneath barrels 92 when carriage 46 is in the maximum rearward position.

Also shown in FIG. 5 is a start button 214 by which the programmed microprocessor is signalled to start the automatic sequence of events for the automatic pipetting apparatus which will be explained in detail below. Lamp 212 provides a visual indication to the user of the automatic pipetting apparatus 10 that the power is turned on.

FIG. 6 illustrates in a cross-sectional view taken along lines 6—6 of FIG. 5 the means by which the carriage is translated with respect to track 34. The track 34 is supported upon base 12 by means of supports 48. The carriage 46 includes slots 49 in its sides on which it slides on tracks 34.

Plate 16 as indicated above is disposed within a notch or valley 47 of the carriage 46. The carriage translation motor 40 is fixed to the base 12 and includes a shaft 42 which is supported by means of shaft supports 44. Pinions 38 secured to shaft 42 have their gears in engagement with racks 36 which are attached to the carriage 46. As the motor 40 is turned in one direction or the other under control of the microprocessor in the electronic module 200 (FIG. 16), the carriage 46 moves in the forward or rearward directions.

FIG. 7 illustrates the pipette assembly 70 looking rearwardly along lines 7—7 of FIG. 3. The mounting blocks 76 are shown secured to the base mounting blocks 78 by means of screws 79. The mounting blocks 76 carry vertical mounting posts 72 as illustrated in FIGS. 7, 10 and 13 and in the top views of FIGS. 8, 11 and 14. The front plates 73 and back plate 83 are secured by means of screws to bearing blocks 76.

A mounting plate 80 is vertically slidably supported about the vertical mounting posts 72. Retainer bearings 74 provide sliding engagement between the posts 72 and vertical bearing blocks 75. The mounting plate 80 is fastened to extensions of bearing blocks 75 by means of screws 81. By reference to FIGS. 7 and 13, it is seen that mounting plate 80 may be moved from its upward position as shown in FIG. 7 to its lower position as shown in FIG. 13 by its attachment to bearing blocks 75 and their sliding engagement on posts 72.

A barrel bar 88 is secured to mounting plate 80 by means of screws 89. Mounted on barrel bar 88 are a plurality of pipette barrels 92 having their heads secured within the tip bar 88 in a manner to be described below. As illustrated in the partial cut away of barrel bar 88, the barrel lock bar 91 secures the lower portions of the barrels 92 to provide stability to the barrels. Guide tips 97 include adjustable screws 95 extending below the bottom edge of the mounting plate 80 which cooperate with the lower surfaces 49 of plate 16 to accurately vertically position the lower tips 93 of barrels 92 with respect to the support medium 20 and blotting paper 30 disposed on lower surface 49 of plate 16. Such adjustment allows the droplets which form on the ends of the tips 93, when plungers 84 are driven downwardly within barrels 92, to "kiss" or be slightly applied either to the support medium or the blotting paper. The droplets on the tips 93 of the barrels 92 are held because of their small size (as small as one micro liter) and surface tension forces of the barrel tips. When the tips are brought to a small distance within the upper surface of the support medium 20 or blotting paper 30, the droplets are relieved of the surface tension holding them to their barrels and are precisely applied to the blotting paper or to the support medium.

Actuator guides 183 are secured to the mounting plate 80 and include grooves 87 in which an actuator plate 84 is inserted for sliding movement upwardly and downwardly with respect to the mounting plate 80. The actuator plate 84 has grooves 85 in which a plunger bar 90 is inserted. The plungers 94 of the microsyringe barrels 92 are secured to the plunger bar 90 and extend within the barrels 92. As illustrated in FIG. 7, the plungers are at their uppermost extent with respect to the barrels 92. The actuator plate 84 is adapted to move downwardly with respect to the mounting plate 80, and through such action, the plunger bar 90 moves downwardly with respect to the barrel bar 88 causing plungers 94 to move downwardly within the barrels 92 thereby forcing any fluid within such barrels outwardly through the tips of the barrels 93 and forming a droplet at the tips of the barrels.

Position signals are generated indicative of the position of the mounting plate 80 with respect to the base 12 and the position of the actuator plate 84 and its plungers 94 with respect to the mounting plate 80. The trip switch 106 mounted on the mounting plate 80 cooperates with the lower stop 115 mounted on the mounting block 76 to provide a lower mounting plate position signal when the mounting plate 80 reaches its lower extent. In a similar way as shown on the right hand side of the mounting plate 80, the upper trip switch 105 is mounted on the mounting plate 80 and is shown tripped by contact with the upper stop 114. The upper trip switch 105 when tripped provides a signal to the microprocessor of electronics module 200 (FIG. 3) indicative that the mounting plate 80 is in its upper position.

The trip switch 108 mounted on actuator guide 86 cooperates with application position cam 100 and wash cam 102. The trip switch 108 is tripped by the application cam 100 when the actuator plate 84 moves upwardly with respect to the mounting plate 80 and the trip switch 108 is tripped by wash cam 102 as the actuator plate 84 moves further upwardly. The down cam 104 trips trip switch 110 mounted on the right hand side actuator guide 86 when the actuator plate 84 reaches its maximum downward travel where the plungers 94 are within the barrels 92.

Figure 9:
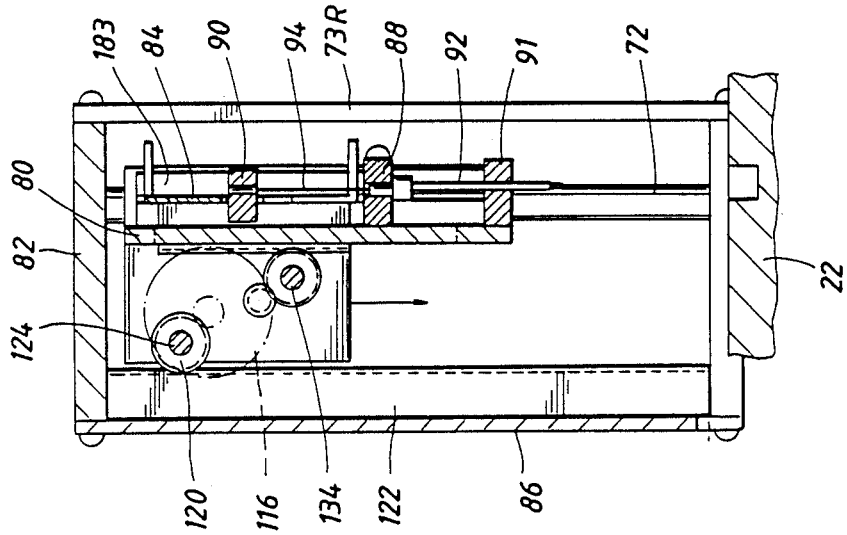
FIG. 9 shows a cross-sectional view taken along lines 9—9 of FIG. 7 and illustrates the relationship between the mounting plate, the tip bar and the plunger bar and the means by which the mounting plate is moved up and down with respect to the base.

FIG. 9 is a cross-sectional view taken along lines 9—9 of FIG. 7 and illustrates the mounting plate 80 and the actuator plate 84 both in their upward positions. Mounting plate motor 116 has driven the mounting plate 80 to the upward position by operation of pinion 120 on rack 122 which is secured to the back plate 86 and to the base of the apparatus.

Turning now to FIG. 10, the pipette assembly 70 is shown with the mounting plate 80 in the downward position but the plunger bar 90 and the plungers 94 are in their upward position with respect to the tip bar 88. The barrels 92 are in a downward position in the wash well for aspirating 5 µl fluid, for example, from the wash well 26.

FIG. 11, a view of the pipette assembly looking downwardly along lines 11—11 from FIG. 10, illustrates the drive mechanism by which the mounting plate 80 is moved up and down with respect to the base. A mounting plate actuator motor 116 is fixed to the mounting plate 80 by means of a mounting screw 117. The output shaft of the motor 116 has a gear 119 fixed to it. Gear 119 is engaged with a left pinion gear 120L which is mechanically coupled to a right pinion gear 120R by means of shaft 124. The shaft is mounted to the mounting plate 80 by shaft mountings 118. Racks 122, fixed to the back plate 86, have their gears in engagement with pinion gears 120L and 120R. As the motor 116 turns in either direction under microprocessor control, the mounting plate 80 is moved upwardly or downwardly with respect to the base and the back plate 86 by the rack and pinion mechanism. The front view (FIG. 10) of the pipette assembly 70 with the mounting plate 80 in a downward position shows the racks 122 visible. The front view also illustrates, with the mounting plate 80 in its maximum downward position, that stop screws 95 of guide tips 94 are slightly above surfaces 49 of the plate 46 indicative that tips 93 are slightly above the top edge 49 of the plate so that droplets which form on the tips may "kiss" the surface 49 and apply sample fluid to the support medium or blotting paper.

Figure 12:
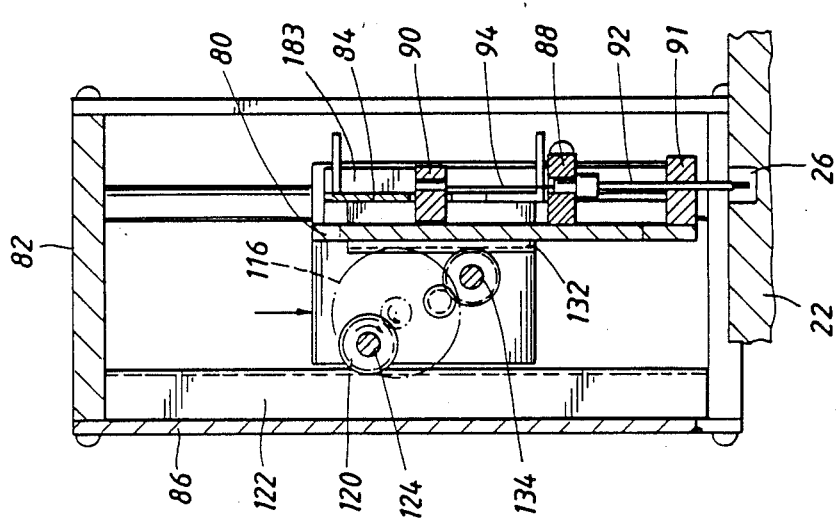
FIG. 12 is a cross-sectional view taken along lines 12—12 of FIG. 10 and illustrates the relationship of the mounting bar after it has been moved downwardly by the rack and pinion system by operation of the motor turning with respect to the frame mounted rack.

FIG. 12 is a cross-sectional view of the pipette apparatus taken along lines 12—12 of FIG. 10 and shows that the mounting plate actuator motor 116 has turned its pinion gear 120 so that the mounting plate 80 has been moved downwardly with respect to the base and the raised portion 22 of the plate 16. Thus, the barrel 92 has been lowered to be within a well of the raised portion 22 of the sample plate. A wash well 26 is illustrated as an example where the barrels 92 of the pipettes have been lowered by the mounting plate 80 and where the fluid from the wash wells have been aspirated into the barrels by virtue of the plungers 94 being pulled upwardly by means of the actuator plate 84. It is apparent from FIGS. 11 and 12 that the mounting plate 80 is translated upwardly and downwardly with respect to the plate 22 by means of the motor 116 turning and causing the pinion 120 to translate upwardly and downwardly on fixed rack 122.

Turning now to FIG. 13, the state of the pipette apparatus 70 is such that the actuator plate 84 has moved downwardly causing the plungers 94 to be inserted back into the barrels 92 thereby positively displacing any fluid which has been aspirated within the barrels either to an application space, a blotter, or to a waste well. It is seen that the trip switch 108 has been returned to a condition such that any upward movement of the actuator plate 84 will be tripped first by the application cam 100 and then the wash cam 102 providing a means for signalling the position of the actuator plate 84 with respect to the mounting plate 80.

FIG. 14, is a downward looking view along lines 14—14 of FIG. 13 and illustrates the drive mechanism by which the actuator plate 84 is translated upwardly and downwardly with respect to the mounting plate 80. A plunger bar actuator plate motor 126 is fixed to the mounting plate 80 by means of a mounting screw 127. The motor 126 includes a gear 128 on its output shaft which is in engagement with pinion gear 130R. Pinion gear 130R is coupled to a pinion gear 130L by means of a shaft 134 which is supported by means of shaft mountings 118 which also supports shaft 124 (see FIG. 11). The actuator plate 84 has actuator plate racks 132 fixed to the rear side thereof which extend through slots 136 in the mounting plate so as to engage the pinions 130L and 130R. As the plunger bar actuator plate motor 126 is caused to turn in either the clockwise or the counterclockwise direction, the actuator plate 84 is caused to move upwardly or downwardly with respect to the mounting plate 80. FIG. 13 shows the slots 136 in the mounting plate 80 through which the actuator plate racks 132 extend.

FIG. 14 also shows the means by which the barrel heads 93 of the barrels 92 are removably fixed to the tip bar 88. The tip bar 88 comprises a receiving bar 138 having slots 140 provided along its front face. The barrel heads 193 are inserted therein and secured by means of a securing bar 139 which holds the barrels vertically in place. The securing bar 139 is secured to the receiving bar 138 by means of screws 141. The barrel lock 91 is similarly constructed as the barrel bar 88. The barrel bar 88 provide a removably securing means by which the barrels 92 may be easily replaced due to wear or breakage.

Figure 15:
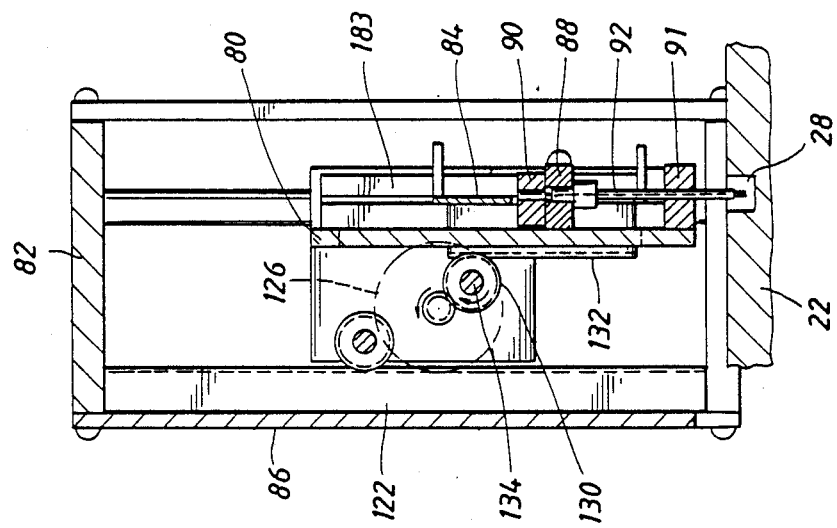
FIG. 15 is a cross-sectional view taken along lines 15—15 of FIG. 13 and illustrates the movement of the actuator plate downwardly with respect to the mounting plate by operation of the rack and pinion system controlling relative movement between the actuator plate and the mounting plate.

FIG. 15 is a cross-sectional view looking along lines 15—15 of FIG. 13 and illustrates the mounting plate 80 in a downward position. The actuator plate 84 has been translated downwardly where the plunger bar 90 is adjacent the tip bar 88. FIG. 15 illustrates the actuator plate racks 132 extending through slots of the mounting plate 80 and their engagement with pinion gear 130 which has been turned by means of the actuator plate motor 126. The barrel 92 is now in a rinse well 28, for example. The plunger 94 has been forced down by means of the actuator plate 84 moving the plunger bar 90 to its lowermost position. Of course, the raised portion of the plate 22 has moved longitudinally with respect to the pipette assembly between the views of FIGS. 12 and 15.

Figure 16:
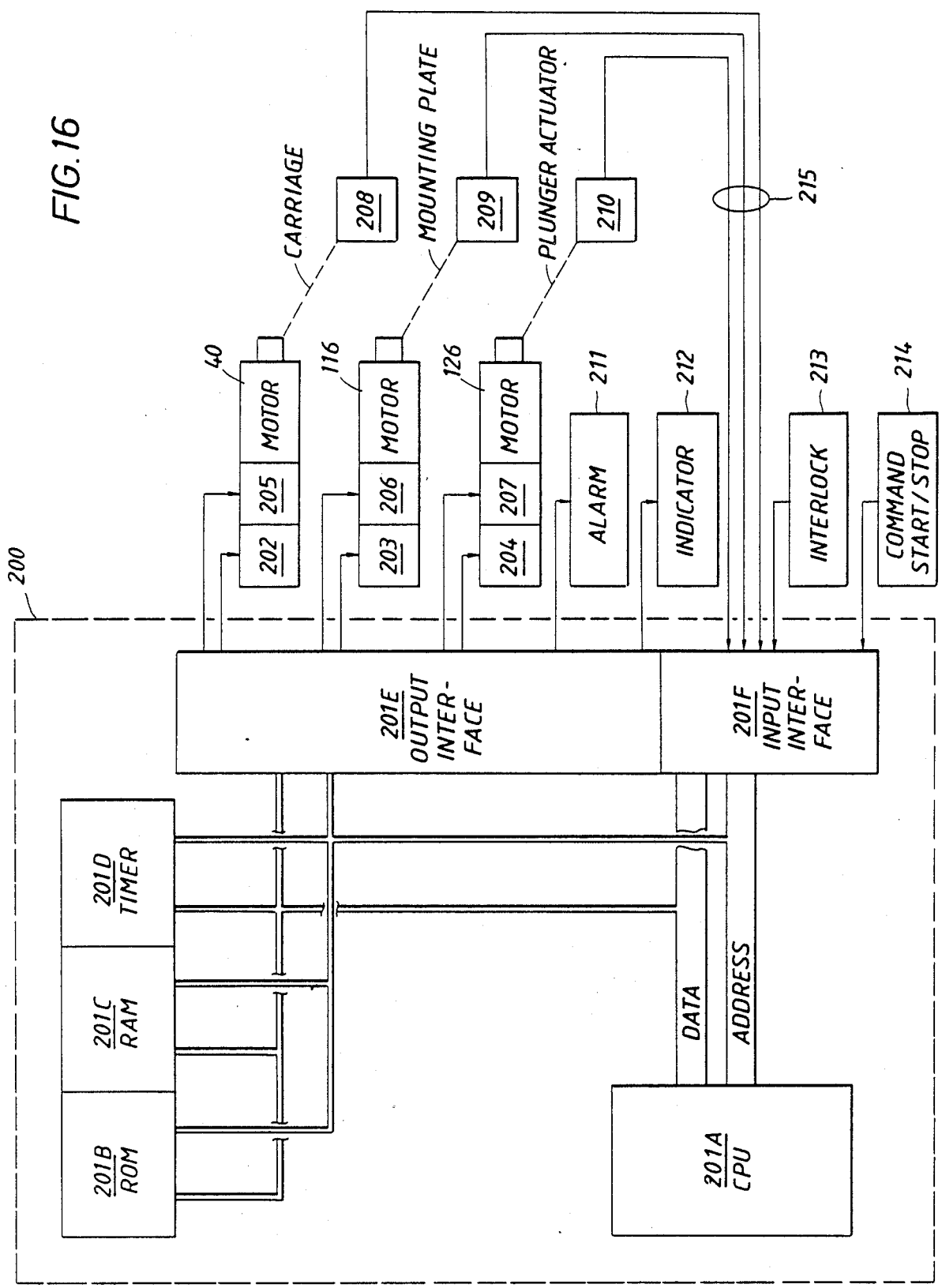
FIG. 16 is a schematic illustration of the microcomputer integrated circuit device receiving signals from position detector circuits associated with the carriage, the mounting plate and actuator plate and applying translation signals to motors for positioning the carriage, the mounting plate and the plunger actuator plate.

FIG. 16 illustrates schematically the means by which the carriage mounting plate and plunger actuator bars are controlled to perform the automatic pipetting operation. The dotted box 200 represents a microcomputer integrated circuit device, preferably a microcircuit No. HD68P0V07 manufactured by the Hitachi Corporation. The circuit includes a central processing unit 201A, a read only memory 201B, a random access memory 201C, a timer 201D, an output interface circuit 201E and input interface circuit 201F. The read only memory circuit 201B includes stored software by which the entire automatic operation is controlled and will be discussed below.

FIG. 16 illustrates the carriage motor 40, the mounting plate motor 116 and the plunger actuator bar motor 126 all under computer control via the motor driver circuits 202, 203, 204 such as circuits UDN-2952B manufactured the SPRAGUE Corporation. These motor driver circuits are used to control the speed of the motor and its direction of rotation. Also provided in conjunction with the motor are electronic motor break circuits 205, 206, 207 which are provided to quickly break the motor's rotation on receipt of a translation signal by the computer 200. Such electronic motor break circuits are preferably 2N6075 Triac circuits.

The position detector circuits 208 represent the circuitry with the trip switches 60 and 62 illustrated in FIG. 5 which indicate the position of the carriage 46 and the sample plate 16 with respect to the pipette assembly.

The position detector circuits 209 represent the circuitry associated with the lower trip switch 106 and the upper trip switch 105 which signal the upward or downward limits of travel of the mounting plate 80 with respect to the base.

The position detector circuits 210 represent the circuitry associated with trip switches 108 and 110 which indicate the relative position of the actuator plate 84 with respect to the mounting plate 80. The signals associated with each of those position detector circuits are represented as being carried by a bundle of electrical leads 215 to the input interface circuitry 201F of computer 200.

The alarm circuit 211 is provided for the apparatus, for example, such as a sounding device EAF14R06C manufactured by Panasonic. Such circuit is activated and a sound is generated to signal faults in the operation of the apparatus or to signal the readiness of the machine Indicator circuit 212 represents an indicatOr lamp 212 as illustrated in FIG. 5 to signal the user that the power is on to the apparatus. The interlock circuit 213 represents the circuitry with carriage interlock switch 65 which indicates the presence or absence of the sample plate on the carriage. Command circuit 214 represents a push button switch used to start or abort the automatic pipetting application process.

In operation, the central processing unit 201A receives the sequence of events instructions from the programs stored in the read only memory 201B. The central processing unit 201A then receives positional information concerning the moving mechanisms of the apparatus by means of reading and decoding the binary coded data present at the input interface 201F which receives information via leads 215 from the position detector circuits 208, 209, 210.

The microprocessor CPU 201A then receives an input command to start or abort the process by means of reading and decoding the binary coded data present at the input interface 201F which is connected to the command circuit 214 which may be the push button 214 illustrated in FIG. 5.

Figure 17:
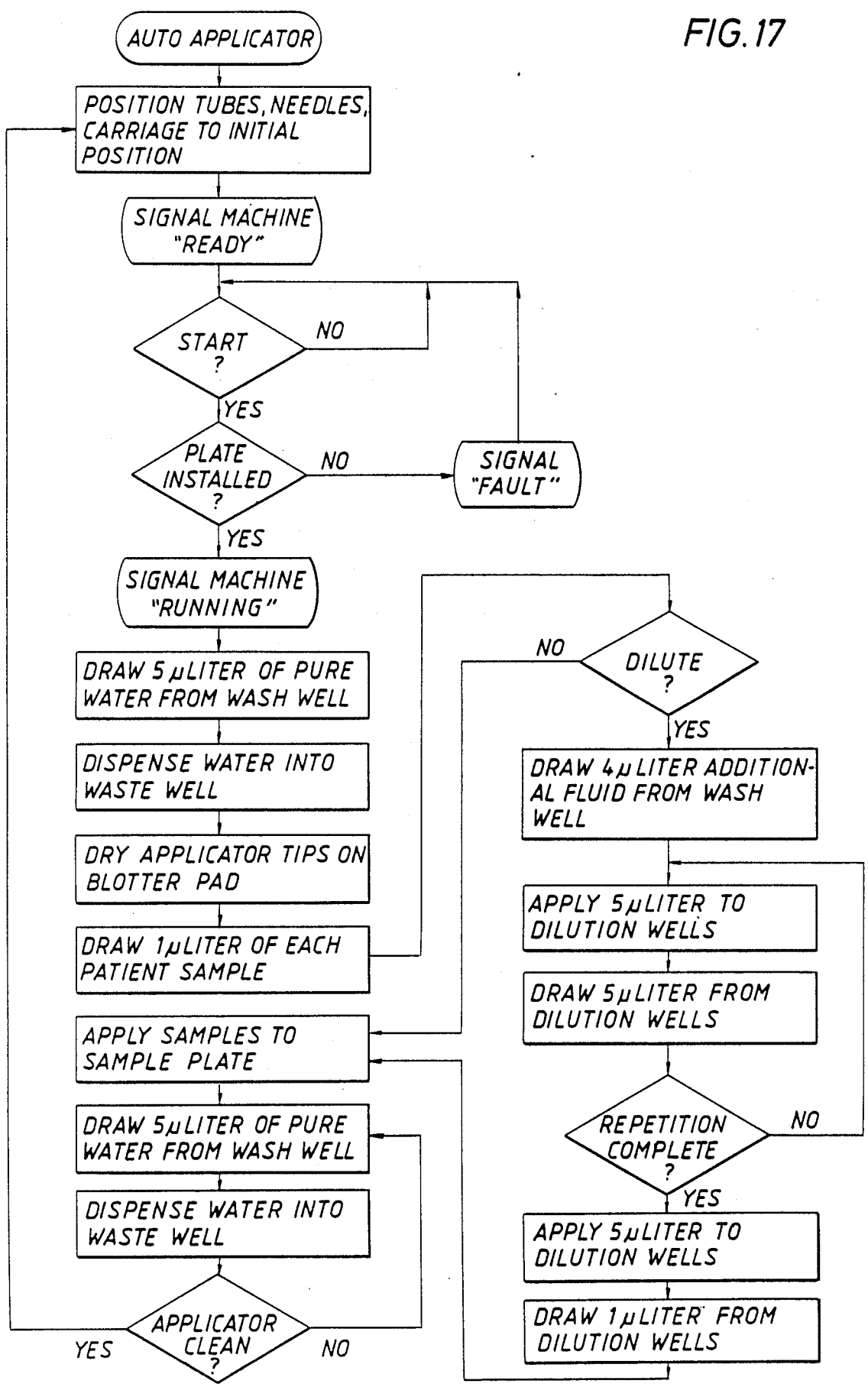
FIG. 17 is a functional flow chart illustrating the stored program in the microcomputer device for automatically washing, blotting, sampling and applying samples to the support medium strip.

FIG. 17 illustrates in flow chart form the operations of the CPU 201A under program control. The CPU 201A determines the validity of a command to start the processing by means of reading and decoding the binary coded data present at the input interface 201F which receives a signal from the interlock circuit 213. This operation insures that the plate 16 is fully inserted into the carriage.

The CPU 201A causes the motors 40, 116 or 126 to turn in the required direction be means of writing the appropriate binary coded data to the output interface circuit 201E which is connected to the motor drive circuits 202, 203 and 204. The microprocessor CPU 201A then causes the mechanism movement to stop precisely when the required location is reached by writing the appropriate binary coded data to the output interface circuit 201E which is connected to the motor drive circuits 202, 203, 204 to disable the drive and then writing the appropriate binary coded data to the output interface 201E which is connected to the motor break circuits 205, 206, 207 to apply electronic breaking.

The microprocessor circuit 201A then signals that the pipetting apparatus is ready or that a plate has been completed or that a failure has occurred by means of writing the appropriate binary coded data to the output interface circuit 201E connected to the alarm circuit 211 to sound an alarm.

The timer 201D of FIG. 16 is used by the microprocessor CPU 201A to determine electrical or mechanical failures of the positioning mechanism. This is accomplished by means of measuring the elapsed time during a command to drive any motor. If the event is not completed within the prescribed length of time, the drive command is aborted and the alarm is activated by means of the microprocessor CPU 201A writing the appropriate binary coded data to the output interface connected to the alarm circuit 211. The timer 201D is also used to determine the repetition rate of the alarm thereby allowing the microprocessor circuit CPU 201A to encript and communicate to the operator the nature of the failure.

As shown in FIG. 17, once the automatic pipetting apparatus of the invention is running, a wide variety of different applications may be achieved. The sequence of operations shown in FIG. 17 is preferred in that first, five microliters of cleansing agent such as distilled water is aspirated into the barrels of the pipettes from the wash well. Next, the water in the barrels is dispensed into the waste well. Then the applicator tips are dried by lowering them to a blotter pad as illustrated in FIG. 5.

Next, the barrels are moved to their upward position with the plungers in their downward position, the carriage is moved rearward and the barrels are lowered into the sample chambers 24. The plungers are raised thereby drawing a small amount of each sample of liquid, for example, patient blood to be tested. Where no dilution of the blood samples is desired, the samples are applied precisely to the cellulose acetate or agarose strip. The barrels are raised again. Again, the carriage is moved forward until the wash well is beneath the barrels and the mounting plate is lowered such that distilled water is again drawn into the barrels and then dispensed into the waste well.

Where dilution of the sample liquids is desired, the sample plate of FIG. 2B may be substituted for that of FIG. 2 and the computer program illustrated by the flow chart of FIG. 17 branches to the dilute routine. A preferred routine for diluting the samples is to draw an additional four micro liters of fluid from the wash well. This action results in each of the barrels being filled with four micro liters of diluting fluid (e.g, water) and one micro liter of blood (or other liquid) sample. Next the entire five micro liters of fluid of each barrel is applied to the respective dilution chambers of the dilution row of the plate of FIG. 2B. This process may be repeated a desired number of times to effect mixing of the sample with the dilution fluid (water). Finally a one micro liter sample of the diluted blood sample is drawn into each barrel according to the description presented previously. The routine then proceeds as described above where the one micro liter of diluted liquid sample is applied to the support medium.

The dilution routine described above is preferred, but other routines may be used to effect good mixing of the blood sample with diluting liquid. For example, a first predetermined amount of liquid sample in each barrel may be applied to the dilution wells. A predetermined amount of wash liquid may then be applied to the dilution wells. After mixing the combination of the wash liquid and liquid sample of the dilution wells, (for example by the mixing technique described above), a small amount of liquid samples is aspirated from the dilution wells and applied to the support medium.

The appendix to this specification includes a source listing of the computer program written in HD68P01V07 Hitachi Assembly language which is stored in the read only memory 201B so as to automatically control the pipetting, cleansing, blotting, diluting (at the operator's option) and other functions described above.

Various modifications and alterations in the described structures will be apparent to those skilled in the art of the foregoing description which does not depart from the spirit of the invention. For this reason, these changes are desired to be included in the appended claims. The appended claims recite the only limitation to the present invention and the descriptive manner which is employed for setting forth the embodiments and is to be interpreted as illustrative and not limitative.

What is claimed is:

1. Apparatus adapted for use with automatic pipetting of liquid samples to be subjected to electrophoresis comprising a sample plate including a lateral row of individual liquid sample chambers and a lateral application space longitudinally separated from said liquid chamber row, said lateral application space having disposed thereon a removable microporous support medium adapted for electrophoretic analysis after a liquid sample has been deposited thereon, said sample plate including an upper portion and a lower portion, said row of individual liquid sample chambers being disposed on said raised portion, said lateral application space being disposed on said lower portion.

2. Automatic pipetting apparatus comprising a base, sample plate mean stationarily disposed on said base, said sample plate means having longitudinal and lateral dimensions, said plate means including a lateral row of liquid sample chambers and a lateral application space longitudinally separated from said liquid chamber row, said lateral application space adapted to receive a microporous support medium, said sample chambers adapted to receive liquid samples, a pipette frame including vertical support means for supporting said frame from said base laterally above said sample plate means, longitudinal translation means for effecting longitudinal movement of said pipette frame between said lateral row of said sample chambers and said lateral application space above said stationarily disposed sample plate means, a mounting plate carried by said pipette frame, vertical translation means for effecting relative vertical movement of said mounting plate and said sample plate means, a plurality of microsyringe barrels having their heads secured in a row to said mounting plate, said barrels spaced corresponding to the spacing of said liquid chambers on said plate, said barrels being hollow with each having a lower tip, a plurality of micro-plungers, each of said plungers disposed in one of said barrels, plunger translation means for moving said plungers vertically within said barrels, signalling means for generating longitudinal signals representative of the relative longitudinal orientation of said pipette frame with respect to said sample plate means, for generating mounting plate signals representative of the vertical orientation of said mounting plate relative to said sample plate means and for generating plunger signals representative of the orientation of said plungers relative to said barrels, and programmed computer means responsive to said longitudinal signals, to said mounting plate signals and to said plunger signals for generating a sequence of control signals to said longitudinal translation means, to said vertical translation means and to said plunger translation means to aspirate a first predetermined amount of liquid from said sample chambers into said respective pipette barrels, and to apply.

a droplet of said liquid samples in each of said pipette barrels onto corresponding spaces of said microporous support medium when placed on said lateral application space of said sample plate by precisely positioning said lower tips of said barrels at a small distance above said microporous support medium, said small distance being smaller than the diameter of a droplet of liquid sample which may be maintained on the end of said tips through surface tension forces of the barrel tips, whereby each droplet slightly touches said microporous support medium and is thereby relieved of its surface tension and is precisely transferred to said microporous support medium from each of said pipette barrels.

* * * * *